United States Patent [19]

Godleski

[11] Patent Number: 5,189,199
[45] Date of Patent: Feb. 23, 1993

[54] PROCESS FOR THE PREPARATION OF 1,4-DISUBSTITUTED 2-BUTENES

[75] Inventor: Stephen A. Godleski, Fairport, N.Y.

[73] Assignee: Eastman Kodak Company, Rochester, N.Y.

[21] Appl. No.: 839,747

[22] Filed: Feb. 20, 1992

Related U.S. Application Data

[63] Continuation of Ser. No. 713,561, Jun. 10, 1991, abandoned, which is a continuation of Ser. No. 239,884, Sep. 2, 1988, abandoned, which is a continuation-in-part of Ser. No. 101,885, Sep. 28, 1987, abandoned.

[51] Int. Cl.$^5$ .................. C07C 67/26; C07C 67/24
[52] U.S. Cl. .................................... 560/93; 560/240
[58] Field of Search ............... 560/240, 93, 200, 112; 260/410.6

[56] References Cited

FOREIGN PATENT DOCUMENTS 0075238 3/1983 European Pat. Off. .
0183042 6/1986 European Pat. Off. .

OTHER PUBLICATIONS

Tsuji, J. et al, Tetrahedron Letters, vol. 22, No. 27 pp. 2575–2578 (1981).
Frost, B. M. et al, J. Am. Chem. Soc., 1985, 107 pp. 6123–6124.
Tsuda, T. et al, J. Org. Chem., 1986, 51, pp. 5216–5221.
Chemical Abstracts, vol. 83, No. 21, Nov. 24, 1975, Abstract 178359a.

*Primary Examiner*—Arthur C. Prescott
*Attorney, Agent, or Firm*—J. Frederick Thomsen; William P. Heath, Jr.

[57] ABSTRACT

A process is disclosed for the preparation of 1,4-dioxy-2-butenes by reacting 3,4-epoxy-1-butene with an oxygen nucleophile in the presence of a Pd(O) complex catalyst.

7 Claims, No Drawings

PROCESS FOR THE PREPARATION OF 1,4-DISUBSTITUTED 2-BUTENES

This is a continuation of copending application Ser. No. 07/713,561 filed on Jun. 10, 1991, which is a continuation of Ser. No. 07/239,884 filed on Sep. 2, 1988, which is a continuation-in-part of Ser. No. 101,885 filed Sep. 28, 1987 abandoned.

FIELD OF THE INVENTION

The invention relates to a process of catalytically converting 3,4-epoxy-1-butene to dioxy substituted 2-butenes. In one aspect, this invention relates to the selective preparation of 1,4-disubstituted 2-butenes.

BACKGROUND

Japanese Kokai SHO 54[1979]-79214 discloses a process for the catalytic synthesis of 2-butene-1,4-diol from a starting material of 3,4-epoxy-1-butene. If the reaction is carried out using only hydriodic acid as a catalyst, the desired reaction product is disclosed to be obtained with selectivity up to about 57%, but with yields in the range of only about 15%–25%. It is suggested that if a transition metal compound is employed in combination with hydriodic acid as a catalyst, the selectivity of the reaction is improved. The term "transition metal compound" is defined as encompassing compounds consisting of group IIIA, IVA, VA, VIA, VIIA, VIII, and IB elements of the fourth, fifth, and sixth period of elements in the periodic table of elements. More specifically, compounds containing ytrrium, lanthanoid elements, titanium, zirconium, vanadium, molybdenum, tungsten, manganese, rhenium, iron, ruthenium, osmium, cobalt, rhodium, iridium, nickel, palladium, platinum, copper, silver, and gold can be employed. The highest yield reported is 57% employing a combination of hydroiodic acid and manganese dioxide. All other reported yields are below 50%.

Japanese Kokai SHO 50[1975]-88514 discloses a non-catalytic process for the preparation of a 4-alkylcarbonyloxy 2-buten-1-ol by first reacting 3,4-epoxy-1-butene with potassium iodide to produce 4-hydroxy-3-iodo-1-butene, followed by reaction with acetic acid.

Tsuji, Kataoka, and Kobayashi, "Regio-selective 1,4-Addition of Nucleophiles to 1,3-Diene Monoepoxides Catalyzed by Palladium Complex", *Tetrahedron Letters*, Vol. 22, No. 27, pp. 2575–2578, 1981, discloses the reaction of 1,3-diene monoepoxides in the presence of $Pd(PPH_3)_4$ with compounds such as dimethylmalonate, acetoacetate, pyrrolidine, 2-methyl-1,3-pentanedione, and allylsulfonyltoluene. In no instances is the formation of a 1,4-dioxy substituted 2-butene taught.

Tsuda, Tokai, Ishida, and Saegusa, "Palladium-Catalyzed Reaction of 1,3-Diene Monoxides with β-Keto Acids, Allylic Alkylation and Isomerization of 1,3-Diene Monoepoxides", *Journal of Organic Chemistry*, 1986, Vol. 51, pp. 5216–5221, is, to the extent pertinent, essentially cumulative in its teachings.

Trost, Urch, and Hung, "Regiochemical Directing Effects in Palladium Catalyzed Alkylations with Polyene Electrophilic Partners", *Tetrahedron Letters*, Vol. 27, No. 41, pp. 4949–4952, discloses the alkylation of complex diene monoxides with carbon nucleophiles in the presence of $Pd(PPh_3)_4$.

Fujinami, Suzuki, Kamiya, Fukuzawa, and Sakai, "Palladium Catalyzed Reaction of Butadiene Monoxide With Carbon Dioxide", *Chemistry Letters*, pp. 199–200, 1985, discloses the conversion of butadiene monoxide to a 3,4-carbonato-1-butene employing $Pd(PPH_3)_4$ as a catalyst.

Palladium catalyzed reactions involving cyclic and acyclic diene monoxides are also reported by the following:

Trost, Lynch, and Angle, "Asymmetric cis-Hydroxylation via Epoxidation-Carboxylation: A Formal Synthesis of (+)-Citreoviral", *Tetrahedron Letters*, Vol. 28, No. 4, pp. 375–378.

Trost and Angle, "Palladium-Mediated Vicinal Cleavage of Allyl Epoxides with Retention of Stereochemistry: A Cis Hydroxylation Equivalent", *J. Am. Chem. Soc.*, 1985, Vol. 107, 6123–6124.

Trost and Molander, "Neutral Alkylations via Palladium(0) Catalysis", *J. Am. Chem. Soc.*, 1981, Vol. 103, pp. 5969–5972.

Deardorff, Myles and MacFerrin, "A Palladium-Catalyzed Route to Mono- and Diprotected cis-2-Cyclopentene-1,4-diols", *Tetrahedron Letters*, Vol. 26, No. 46, pp. 5615–5618 (1985).

Deardorff, Shambayati, Linde and Dunn, "Palladium-Catalyzed Syn, 1,4-Additions of Silyl-Derived Carboxylates and Phenoxides to Cyclopentadiene Monoepoxide. A Stereo- and Regiocontrolled Route to Differentially Protected cis-2-Cyclopentene-1,4-diols", *J. Org. Chem.*, 1988, Vol. 53, pp. 198–191.

As the above-described prior art makes clear, the preparation of 1,4-dioxy substituted 2-butene compounds from 3,4-epoxy-1-butene by catalytic reactions has been generally known prior to the present invention. However, conventional processes have exhibited a variety of disadvantages. For example, many processes, though producing the desired 1,4-dioxy substitution pattern also produce large amounts of undesired 1,2-dioxy isomers.

The highest levels of selectivity in achieving the desired 1,4-dioxy substitution pattern (<60%) have been achieved employing hydriodic acid or alkali metal iodide salts. In either case, a highly corrosive acid reaction medium is created. Refluxing or otherwise heating the reaction medium exacerbates problems of equipment corrosion.

SUMMARY OF THE INVENTION

The present invention makes available for the first time a high yield process for the preparation of 1,4-disubstituted 2-butenes employing 3,4-epoxy-1-butene as a starting material. The invention process employs a catalyst that exhibits no significant attack on the materials, such as glass, steel, brass, rubber, and structural plastics, conventionally used to interface with reaction media in large scale synthetic environments. Further, the process of the present invention does not require heating of the reaction medium, which both reduces the cost and simplifies the equipment required for performing the synthetic process of the invention.

In one aspect this invention is directed to a process comprised of reacting 3,4-epoxy-1-butene with an oxygen-nucleophile, e.g., an alcohol, carboxylic acid, anhydride or substituted hydroxy, carboxy or anhydride containing compound in the presence of a catalyst to produce a 1,4-dioxy substituted 2-butene, where at least one oxy substituent is the oxy residue of the oxygen nucleophile. The process is particularly characterized in that the catalyst is a Pd(0) complex, e.g., a complex of palladium with four phosphine ligands, and the oxygen

DETAILED DESCRIPTION OF INVENTION

The process of the present invention is concerned with the production of 1,4-disubstituted derivatives of 3,4-epoxy-1-butene having the following structural formula:

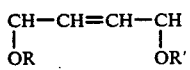

wherein R is $C_1$–$C_{20}$ alkyl or substituted alkyl, $C_4$–$C_{10}$ aromatic and heteroatom-substituted aromatic moieties, $C_1$–$C_{20}$ acyl, or

wherein Ar is a $C_4$–$C_{10}$ aromatic or heteroatom-substituted aromatic moiety; and R′=R or H;

with the provision that neither R nor R′ contain any activated methylene or methine groups. As herein employed the term "activated methylene or methine group" refers to a methylene or methine (monosubstituted methylene) group interposed between two strongly electron withdrawing groups:

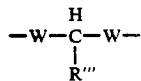

where

R‴ can be hydrogen or any hydrocarbon group, including substituted hydrocarbon groups, and W is a strongly electron withdrawing group, such as carbonyl, sulfonyl, nitrile, or nitro. If a dicarboxylic acid or carboxy substituted ester containing an active methylene or methine group is reacted with 3,4-epoxy-1-butene in the presence of a catalyst such as a complex of palladium within the range of two-four phosphine ligands, formation of the desired 1,4-dioxy substituted 2-butene reaction product is inhibited. Instead, reaction occurs by displacement of hydrogen from the methylene or methine group linking the strong electron withdrawing groups. This is illustrated by the teachings of the art cited above for the case in which the strongly electron withdrawing groups are carbonyl groups. Thus, propandioic (malonic) acid is specifically excluded from the contemplation of the invention.

Substituted derivatives contemplated include halogens, carbonyl, sulfonyl, nitrile, and nitro moieties. These are contemplated where their placement in the molecule does not produce an activated methylene or methine group.

The invention process is accomplished by reacting the 3,4-epoxy-1-butene starting material with an oxygen nucleophile in the presence of a catalyst comprising a Pd(0) complex, e.g., a complex of palladium within the range of two up to four phosphine ligands, or a Pd(0) precursor, i.e., a palladium compound which can be reduced to Pd(0) under the reaction conditions.

The oxgen nucleophiles contemplated for use in the practice of the invention are alcohols, carboxylic acids, anhydrides, and substituted hydroxy, carboxy, or anhydride containing compounds.

As employed herein the term oxygen nucleophile refers to an optionally substituted hydrocarbyl radical having at least one hydroxy moiety, e.g., alcohols, carboxylate moiety, e.g., carboxylic acids, or compounds capable of the in situ formation of carboxylate anions, e.g., anhydrides.

The term "alcohol" indicates an optionally substituted hydrocarbon having one or more hydroxy substituents. Primary, secondary, and tertiary alcohols are contemplated, such as mono-alcohols as well as polyhydroxy variants—e.g., alkandiols, alkantriols, alkantetrols, etc. Broadly, alcohols having up to about 20 carbon atoms are contemplated to be useful in the practice of the present invention. Preferred alkanols are those containing from about 1 up to 12 carbon atoms, with alkanols having 1 up to 6 carbon atoms being most preferred.

Exemplary of preferred aliphatic alcohols are methanol, ethanol, 1-propanol, 2-propanol, 1-propen-2-ol, 1-butanol, 2-butanol, 2-methyl-2-propanol, 1-pentanol, 2-pentanol, 3-pentanol, 3-methyl-1-butanol, 1,2-ethandiol (ethylene glycol), 1,2,3-propantriol (glycerol), i-1,2,3,4-butantetrol (i-erythritol), and 2,2-dihydroxymethyl-1,3-propandiol (pentaerythritol).

Aromatic alcohols contemplated to be useful in the practice of the present invention include those containing one or more aromatic rings having one or more hydroxy substituents or hydroxy-substituted hydrocarbyl substituents. Preferred aromatic alcohols are those containing one or more hydroxy substituted $C_1$–$C_6$ alkyl moieties as substituents of an aromatic nucleus containing from 6 to 10 carbon atoms—e.g., a phenyl or naphthyl nucleus. Viewed another way, exemplary aromatic alcohols can be variants of the aliphatic alcohols mentioned above, differing merely by the inclusion of one or more aromatic rings containing from 6 to 10 carbon atoms (e.g., phenyl or naphthyl rings) as substituents. Exemplary of aromatic alcohols are benzyl alcohol, 2-phenylethanol, cinnamyl alcohol, benzohydrol, and triphenylcarbinol.

Phenolic alcohols are also contemplated for use in the practice of this invention. As herein defined the term "phenolic alcohol" refers to a hydroxy substituted carbocyclic aromatic ring. The carbocyclic aromatic ring preferably contains from 6 to 10 carbon atoms (e.g., phenyl or naphthyl). Exemplary of preferred phenolic alcohols are hydroxybenzene (phenol), 1,2-benzenediol (pyrocatechol), 1,3-benzenediol (resorcinol), 1,4-benzenediol (hydroquinone), 1,2,3,-benzenetriol (pyrogallol), 1,3,5-benzenetriol (phloroglucinol), 2-hydroxytoluene (o-cresol), 1-naphthol, and 2-naphthol.

There are additional alcohols contemplated for use in the practice of the present invention which fit within more than one of the above categories, such as 1-hydroxy-2-(4-hydroxyphenyl)ethane (tyrosol), which is both an aromatic alcohol and a phenolic alcohol.

The term "carboxylic acid" as herein employed indicates a hydrocarbon or substituted hydrocarbon which contains a carboxyl [—C(O)OH] group as a carbon atom substituent. Simple aliphatic monobasic carboxylic acids, such as alkanoic acids of from 1 to 20 carbon atoms are contemplated—e.g., methanoic (formic), ethanoic (acetic), propanoic (propionic), butanoic (butyric), and pentanoic (valeric) acids. Saturated aliphatic dibasic carboxylic acids, such as alkanedioic acids of from 1 to 20 carbon atoms are also contemplated—e.g., ethanedioic (oxalic), butanedioic (succinic), pentanedioic (glutaric), and hexanedioic (adipic) acids. Unsaturated mono and dibasic carboxylic acids containing from 1 to 20 carbon atoms are also contemplated—e.g., propenoic (acrylic), 2-methylpropenoic (methacrylic), trans-2-butenoic (crotonic), cis-2-butenoic (isocrotonic), and 3-butenoic (vinylacetic) acids.

Aromatic carboxylic acids are also contemplated, such as those containing a 6 to 10 carbon atom (e.g., phenyl or naphthyl) aromatic nucleus substituted with at least one carboxylic acid moiety containing from 1 to about 10 carbon atoms. Exemplary of such aromatic carboxylic acids are benzoic, phenylethanoic (α-toluic), 3-phenylpropanoic (hydrocinammic), trans-3-phenylpropenoic (cinnamic), benzenehexacarboxylic (mellitic), 2-methylbenzoic (o-toluic), 3-methylbenzoic (m-toluic), 4-methylbenzoic (p-toluic), 1-naphthalenecarboxylic (αnaphthoic), and 2-naphthalenecarboxylic (β-naphthoic) acids. Specifically contemplated dibasic aromatic carboxylic acids are the phthalic acids 1,2-benzenedicarboxylic (phthalic), 1,3-benzenedicarboxylic (isophthalic), and 1,4-benzenedicarboxylic (terephthalic) acid.

Anhydrides contemplated for use in the practice of the present invention include symmetrical and unsymmetrical anhydrides of the structure

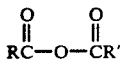

wherein each of R and R' can independently have 1 to 20 carbon atoms and be alkyl, aromatic or heteroatom-substituted aromatic moieties, aralkyl, alkaryl, and the like. Exemplary anhydrides include acetic anhydride, phthalic anhydride, and the like.

Both the alcohols, carboxylic acids, and anhydrides contemplated in the practice of the present invention can contain other substituents that do not interfere with the described reaction, such as, for example, halogens, carbonyl, sulfonyl, nitrile, and nitro moieties are contemplated where their placement in the molecule does not produce an activated methylene or methine group. In addition, additional hydroxy, alkoxy, and aryloxy substituents can be present, if desired. Examples of such acids are β-hydroxyacetic (glycolic), citric, o-hydroxybenzoic (salicylic), m-hydroxybenzoic, p-hydroxybenzoic, p-methoxybenzoic (anisic), 3,4,5-trihydroxybenzoic (gallic), and 4-hydroxy-3,5-dimethoxybenzoic (syringic) acids.

In addition to the substituted variations of carboxylic acids and alcohols described above, esters of these alcohols and carboxylic acids having at least one free hydroxy or carboxyl [—C(O)OH] moiety or substituent are also contemplated for use in the practice of the present invention. Such esters can be viewed as the partial esters of any of the alcohols or carboxylic acids useful in the practice of this invention as described above, containing two or more hydroxy or carboxy groups. Partial esters of any alcohol satisfying the requirements of this invention with any dibasic carboxylic acid satisfying the requirements of this invention are particularly contemplated. Similarly, partial esters of any of the carboxylic acids satisfying the requirements of this invention with any dihydroxy alcohol satisfying the requirements of this invention are particularly contemplated. When a dihydroxy alcohol is esterified with a dibasic carboxylic acid, an ester can be created which contains either free carboxy groups or free hydroxy groups, merely by varying the ratio of acid to alcohol present during esterification.

A wide range of hydroxy and/or carboxy substituted esters are useful in the practice of this invention. The following are exemplary of contemplated hydroxy or carboxy substituted esters: methyl glycolate, 2-hydroxyethyl acetate, glycerol diacetate, methyl hemioxalate, di(2-hydroxyethyl) succinate, and di(6-hydroxyhexyl) terephthalate.

It is appreciated that the nucleophiles identified above can, if desired, be further substituted with any one or combination of groups that do not interfere with the formation of 1,4-disubstituted-2-butenes. For example, halogen (i.e., fluro, chloro, bromo, and iodo) substituents are specifically contemplated. In the extreme case one or all of the hydrogen atoms of the oxygen nucleophiles contemplated by the present invention can be replaced by halogens. Halogen substituted, particularly chloro and bromo substituted, aromatic hydrocarbon moieties are contemplated. Carbonyl, sulfonyl, nitrile, and nitro moieties are also contemplated so long as their placement in the molecule does not produce an activated methine methylene moiety. Still other non-interfering substituents will be apparent to those skilled in the art having access to the teachings of this invention.

The catalyst employed for the invention reaction is a Pd(0) complex, e.g., complex of palladium within the range of about two up to four phosphine ligands. It is important to note that in such a complex the palladium is in its zero oxidation state. Those of skill in the art recognize that Pd(0) can be generated in a variety of ways, such as for example, by treatment of a bis(phosphino) palladium salt with hydrazine, carbon monoxide, a metal alkoxide, an aluminum alkyl, an alcohol or an amine. A particularly convenient way to prepare Pd(0) complexes is to generate them in situ by subjecting a palladium compound to the appropriate reaction conditions, e.g., reduction of $(Ph_3P)_2PdCl_2$ by one of the components of the reaction system, such as an alcohol or an olefinically unsaturated moiety.

The presently preferred source of Pd(0) complex is a complex of palladium with four phosphine ligands. Each phosphine ligand provides a trisubstituted phosphorus atom coordinated with the palladium atom. Preferably, at least two of the three substituents are phenyl moieties. The remaining substituent can be chosen from among a wide variety of hydrocarbons. Thus, in its most general form the preferred palladium (0) complex can be represented by the formula:

$$Pd(PPh_2R'')_4$$

where each R'' is independently a hydrocarbyl moiety, and can optionally be a substituted hydrocarbyl moiety, preferably with no more than one containing more than 6 carbon atoms because of the ready availability of such materials.

In a specifically preferred form, each R'' is phenyl.

In another preferred form, each R can be aliphatic hydrocarbons, such as alkyl or alkylene of from 1 to 6 carbon atoms. In one preferred form of the catalyst two phosphine ligands are joined through a linking moiety to produce a bidentate ligand, for example, by employing the alkylene moiety as represented by Formula II:

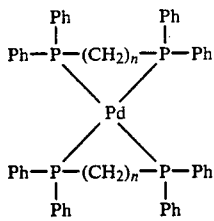

where n is an integer of from 1 to 6.

In another preferred embodiment of the present invention, bidentate ligands of the general formulae

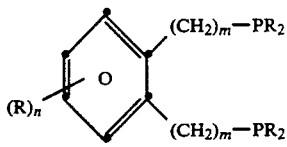

wherein n can vary from 0–4, and each m can vary from 1–3; and

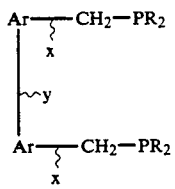

wherein the x bonds and the y bonds are on adjacent ring atoms of the aromatic moieties.

Those of skill in the art recognize that Pd(0) complexes can also be stabilized by other ligands, such as, for example olefins, phosphites and the like.

In another preferred form, the palladium (0) complex is supported on a polymer substrate. That is, the palladium complex forms a pendant group of repeating units of a polymer. In this form, one substituent of at least one of the phosphine ligands is a repeating unit of a polymer. Coordination of the palladium complex to a polymer substrate offers the advantage of protecting the catalyst against loss in use. An example of a commercially available palladium complex supported on a polymer substrate is polymer supported tetrakistriphenylphosphinepalladium (0), Catalog #24815-0, available from Aldrich Chemical Co. Inc.

When the oxygen nucleophile reactant is a liquid, it can be employed as a solvent for the 3,4-epoxy-1-butene reactant. In this instance only the catalyst and the two reactants are required.

If desired, a separate solvent for the reactants can be employed. Any of a wide variety of common polar, aprotic liquid solvents can be selected, such as tetrahydrofuran, benzene, toluene, dimethylformamide, dimethylsulfoxide, chloroform, dichloromethane, acetonitrile, and acetone. Since water will itself react with 3,4-epoxy-1-butene in the presence of the palladium catalyst, it is preferred that the solvent employed for the reaction be relatively water-free.

While the oxygen nucleophile can be incorporated in a solvent up to its solubility limit, it is generally most convenient to work with concentrations of from about 0.1 to 5 molar, preferably from about 0.5 to 2 molar. Since no separate solvent is required where the oxygen nucleophile is itself capable of acting as a solvent, it is apparent that higher concentrations are possible. Lower concentrations are also useful, but are normally avoided absent some specific advantage resulting from further dilution. It has been found that, in general, high concentrations of oxygen-nucleophile lead to enhanced selectivity to 1,4-addition products, while low concentrations of oxygen-nucleophile lead to exhanced selectivity to 1,2-addition products.

The proportions of the reactants and the catalyst can be varied widely while obtaining the desired reaction products in high yield. Since the catalyst contains a precious metal, it is generally preferred to employ the catalyst in low concentrations. Catalyst concentrations as low as 0.01 mole percent, based on 3,4-epoxy-1-butene, are contemplated, with catalyst concentrations preferably being at least 0.05 mole percent, optimally at least 0.1 mole, based on 3,4-epoxy-1-butene, being preferred. The catalyst concentration is normally less than 5 mole percent, preferably less than 2 mole percent, based on 3,4-epoxy-1-butene.

The mole ratio of the oxygen nucleophile to 3,4-epoxy-1-butene can be varied over wide ranges. Mole ratios of from 1:10 to 10:1, preferably 1:5 to 5:1, are contemplated. When it is desired to maximize the conversion of the 3,4-epoxy-1-butene, a stoichiometric excess of the remaining reactant or reactants should be present. Thus, an optimum ratio range is considered to be from 3:1 to 4:1 of the oxygen nucleophile to 3,4-epoxy-1-butene.

The conversion of 3,4-epoxy-1-butene can be achieved at or below room temperature. It is, in fact, preferred to chill the oxygen nucleophile to a temperature in the range of −30° up to 20° C. with a temperature in the range of −10° up to 0° C. being most preferred prior to addition thereto of the 3,4-epoxy-1-butene to control heating during mixing. Mild heating (e.g., up to about 50° C.) to accelerate reactions can be undertaken, but is not preferred.

EXAMPLES

The following examples further illustrate the practice of the invention.

EXAMPLE 1

Reaction of Butadiene Monoxide and Methanol

Tetrakis(triphenylphosphine)palladium (0.5 g, 0.43 mmol) and 3.45 mL (3.0 g, 0.043 mol) of butadiene monoxide were dissolved in 20 mL of methanol. The reaction mixture was stirred 18 hours at room temperature, and then concentrated at reduced pressure. The concentrate was distilled at 40°-55° C., 1 mm pressure, yielding 4.2 g (96%) of a colorless oil which consisted of a 3:1 ratio 1-hydroxy-4-methoxy-but-2-ene (mixture of E and Z isomers) and 4-hydroxy-3-methoxy-but-1-ene.

$^1$H NMR (CDCl$_3$) 4-hydroxy-3-methoxy-but-1-ene: 5.6 (m, 1H); 5.22 (m, 2H); 3.7 (m, 1H); 3.5 (m, 2H); 3.3 (s, 3H); 2.2 (br s, 1H), 1-hydroxy-4-methoxy-but-2-ene: 5.8 (m, 2H); 4.2 (m, 2H); 3.9 (d, J=6 Hz, 2H); 3.3 (s, 3H); 2.2 (br s, 1H).

EXAMPLE 2

Reaction of Butadiene Monoxide and n-Butanol

Tetrakis(triphenylphosphine)palladium (0.4 g, 0.35 mmol) was dissolved in 20 mL of n-butanol and the solution was cooled to 0° C. Butadiene monoxide (2.3 mL, 2.0 g, 0.028 mol) was then added dropwise and the solution was allowed to warm to room temperature. The reaction mixture was stirred at room temperature 18 hours, then fractionally distilled at reduced pressure yielding 4.0 g (90%) of a 4:1 mixture of 1-hydroxy-4-butoxy-but-2-ene:4-hydroxy-3-butoxy-but-1-ene (bp 75°-120° C., 1 mm).

$^1$H NMR (CDCl$_3$) 4-hydroxy-3-butoxy-but-1-ene: 5.65 (m, 1H); 5.25 (m, 2H); 3.8 (m, 2H); 3.5 (m, 3H); 3.3 (m, 1H); 2.3 (br s, 1H); 1.55 (m, 2H); 1.4 (m, 2H); 0.9 (t, J=6 Hz,3H), 1-hydroxy-4-butoxy-but-2-ene: 5.85 (m, 2H); 4.2 (d, J=8 Hz, 2H); 4.0 (d, J=8 Hz, 2H); 3.45 (m, 2H); 2.2 (br s, 1H); 1.55 (m, 2H); 1.4 (m, 2H); 0.9 (t, J=6 Hz, 3H).

EXAMPLE 3

Reaction of Butadiene Monoxide and Ethanol

Tetrakis(triphenylphosphine)palladium (1.0 g, 0.86 mmol) was dissolved in 1 L of ethanol and the reaction mixture was cooled to 0° C. Butadiene monoxide (160 g, 2.28 mol) was then added dropwise. The solution was allowed to warm to room temperature, and was stirred 18 hours. Fractional distillation at reduced pressure yielded a 3:1 ratio of 1-hydroxy-4-ethoxy-but-1 [2]-ene:4-hydroxy-3-ethoxy-but-1-ene (161 g, 61%, bp 45°-70° C.; 1 mm).

$^1$H NMR (CDCl$_3$) 1-hydroxy-4-ethoxy-but-2-ene: 5.8 (m, 2H); 4.1 (d, J=6 H); 3.95 (d, J=6 Hz, 2H); 3.45 (q, J=8 Hz, 2H); 2.5 (br s, 1H); 1.2 (t, J=8 Hz, 3H), 4-hydroxy-3-ethoxy-but-1-ene: 5.7 (m, 1H; 5.2 (m, 2H); 3.65-3.3 (m, 5H); 2.5 (br s, 1H); 1.2 (t, J=8 Hz, 3H).

EXAMPLE 4

Reaction of Butadiene Monoxide with Acetic Acid

Acetic acid (0.82 mL, 14.3 mmol) was added to a suspension of 0.4 g polymer tetrakis(triphenylphosphine)palladium (O) (Aldrich Catalog #24815-0) in 20 mL of THF, followed by 1.15 mL (1.0 g, 14.3 mmol) butadiene monoxide. The mixture was stirred 36 hours at room temperature. The polymer bound catalyst was then removed by filtration and the filtrate was concentrated at reduced pressure. GLC analysis of the products indicated at 1:1 ratio of 1-acetoxy-4-hydroxy-but-2-ene: 3-acetoxy-4-hydroxy-but-1-ene. Distillation at reduced pressure gave 1.7 g (91%) of this product mixture.

$^1$H NMR (CDCl$_3$) 1-acetoxy-4-hydroxy-but-2-ene: 5.82 (m, 2H); 4.7 (d, J=8 Hz, 2H); 4.25 (d, J=8 Hz, 2H); 2.8 (br s, 1H); 2.05 (s, 3H), 3-acetoxy-4-hydroxy-but-1-ene: 5.82 (m, 1H); 5.35 (m, 3H); 3.75 (m, 2H); 2.4 (br s, 1H); 2.05 (s, 3H).

EXAMPLE 5

Reaction of Butadiene Monoxide and Phenol

Tetrakis(triphenylphosphine)palladium (0.4 g, 0.35 mmol) and phenol were dissolved in 70 mL THF and the solution was cooled to 0° C. Butadiene monoxide (5.5 mL, 50 mmol) was then added, and the reaction was allowed to warm to room temperature. After 2 hours at room temperature, GLC analysis indicated that phenol was no longer present, and that two products were obtained in a 1:4 ratio (1-hydroxy-4-phenoxy-but-2-ene: 4-hydroxy-3-phenoxy-but-1-ene). The solvent and excess butadiene monoxide were removed at reduced pressure, and the residue was chromatographed on silica gel (ether:hexane; 1:1 eluant) giving pure samples of each product in a combined yield of 91%.

$^1$H NMR (CDCl$_3$ 4-hydroxy-3-phenoxy-but-1-ene: 7.6 (m, 2H); 7.2 (m, 3H); 6.1 (m, 1H); 5.6 (m, 2H); 5.0 (m, 1H); 4.05 (m, 2H); 2.6 (br s, 1H), 1-hydroxy-4-phenoxy-but-2-ene: 7.6 (m, 2H); 7.2 (m, 3H); 6.1 (m, 1H); 4.6 (m, 2H); 4.25 (m, 2H); 2.15 (br s, 1H).

EXAMPLE 6

Reaction of Butadiene Monoxide with Terephthalic Acid

Terephthalic acid (2.4 g, 14.3 mmol) was suspended in 20 mL dimethylformamide, followed by Pd(PPh$_3$)$_4$ (0.4 g, 0.35 mmol) and butadiene monoxide (2.3 mL, 2.0 g, 28.6 mmol). The reaction mixture was stirred 48 hours at room temperature and then partitioned between 200 mL of aqueous brine and 200 mL of ethyl acetate. The organic layer was separated and washed three times with aqueous brine, then dried over anhydrous sodium sulfate and concentrated at reduced pressure.

$^1$H NMR of the resulting solid indicated that the major constituent of the product mixture was the desired di-[1-(4-hydroxy-2-butenyl)] terephthalate with lesser amounts of di-[2-(1-hydroxy-4-butenyl)] terephthalate and 1-(4-hydroxy-2-butenyl), 2-(1-hydroxy-4-butenyl) terephthalate.

EXAMPLE 7

Reaction of Butadiene Monoxide with Acetic Anhydride

Tetrakis(triphenylphosphine) palladium (1.8 g, 0.5 mmol) was dissolved in 50 mL THF, followed by acetic anhydride (4.05 mL, 14.3 mmol) and butadiene monoepoxide (3.45 mL, 14.3 mmol). The butadiene epoxide was converted to a mixture of 1,4-diacetoxy-but-2-ene and 3,4-diacetoxy-but-1-ene in quantitative yield in 2 h at rt. The products were found to equilibrate under the reaction conditions, eventually yielding a 75:25 ratio, favoring the 1,4-isomer (determined by glc). The solvent was removed under reduced pressure and the resulting oil was distilled at ~0.8 mm Hg pressure providing 7.0 g (95%) of a mixture of diacetoxybutenes.

$^1$H NMR (CDCl$_3$) 1,4-Diacetoxy-but-2-ene, 4:1 mixture of E:Z isomers, E: 5.9(t,J=8 Hz,2H); 4.6(d,J=8 Hz,2H); Z: 5.78(t,J=8 Hz,2H); 4.7(d,J=8 Hz,2H); 2.05(s,3H). 3,4-Diacetoxy-but-1-ene: 5.8(m,1H); 5.5(m,1H); 5.3(m,2H); 4.08(m,2H); 2.04(s,3H); 2.02(s,3H).

The invention has been described in detail with particular reference to preferred embodiments thereof, but it will be understood that variations and modifications can be effected within the spirit and scope of the invention.

I claim:

1. Process for the preparation of compounds of the structure:

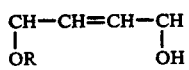

wherein R is $C_1$-$C_{20}$ alkyl or substituted alkyl or $C_4$-$C_{10}$ aromatic moieties; which comprises contacting 3,4-epoxy-1-butene with an alcohol in the presence of a catalytic amount of a palladium catalyst comprising Pd(O) complexed with two to four phosphine ligands.

2. Process according to claim 1 wherein R is alkyl of up to about 12 carbon atoms or alkyl of up to about 6 carbon atoms substituted with phenyl; which comprises contacting 3,4-epoxy-1-butene with an alkanol of up to about 12 carbon atoms or a phenyl-substituted alkanol of up to about 6 carbon atoms in the presence of a catalytic amount of a catalyst comprising Pd(O) complexed with two to four phosphine ligands having the structure:

(phenyl)$_2$PR'' wherein R'' is hydrocarbyl of up to 6 carbon atoms.

3. A process in accordance with claim 1 wherein said alcohol is an alkanol containing from 1 to 20 carbon atoms.

4. A process in accordance with claim 1 wherein said alcohol is a phenolic alcohol.

5. A process in accordance with claim 4 wherein said alcohol is phenol.

6. Process for the preparation of compounds of the structure:

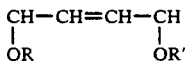

wherein R is alkyl of up to 12 carbon atoms, alkyl of up to about 6 carbon atoms substituted with phenyl, alkanoyl of up to about 20 carbon atoms; and R' is hydrogen or alkanoyl of up to about 20 carbon atoms; which comprises contacting 3,4-epoxy-1-butene with an oxygen nucleophile selected from an alkanol of up to about 12 carbon atoms, a phenyl-substituted alkanol of up to 6 carbon atoms, a carboxylic acid of up to about 20 carbon atoms or a carboxylic anhydride having up to about 40 carbon atoms in the presence of a catalytic amount of a palladium catalyst comprising Pd(O) complexed with two to four phosphine ligands.

7. Process according to claim 6 wherein R is alkyl of 1 to 6 carbon atoms, or acetyl and R' is hydrogen or acetyl; which comprises contacting 3,4-epoxy-1-butene with and alkanol of up to 6 carbon atoms, acetic acid or acetic anhydride in the presence of a catalytic amount of a catalyst comprising Pd(O) complexed with two to four phosphine ligands having the structure:

(phenyl)$_2$PR'' wherein R'' is hydrocarbyl of up to 6 carbon atoms.

* * * * *